United States Patent [19]

Robinson et al.

[11] Patent Number: 4,975,581

[45] Date of Patent: Dec. 4, 1990

[54] METHOD OF AND APPARATUS FOR DETERMINING THE SIMILARITY OF A BIOLOGICAL ANALYTE FROM A MODEL CONSTRUCTED FROM KNOWN BIOLOGICAL FLUIDS

[75] Inventors: Mark R. Robinson; Kenneth J. Ward; Robert P. Eaton; David M. Haaland, all of Albuquerque, N. Mex.

[73] Assignee: University of New Mexico, Albuquerque, N. Mex.

[21] Appl. No.: 369,217

[22] Filed: Jun. 21, 1989

[51] Int. Cl.⁵ .......................................... G01N 21/35
[52] U.S. Cl. .................................. 250/339; 128/633; 128/634; 250/343; 364/498
[58] Field of Search .............. 250/339, 252.1 A, 343; 364/498; 128/633, 634

[56] References Cited

U.S. PATENT DOCUMENTS

| | | | |
|---|---|---|---|
| 3,973,118 | 8/1975 | LaMontagne | 250/226 |
| 4,169,976 | 10/1979 | Kaiser | 356/39 |
| 4,427,889 | 1/1984 | Müller | 250/339 |
| 4,509,522 | 4/1985 | Manuccia et al. | 128/634 |
| 4,642,778 | 2/1987 | Hieftje et al. | 364/498 |
| 4,798,954 | 1/1989 | Stevenson | 250/341 |
| 4,800,279 | 1/1989 | Hieftje et al. | 250/339 |
| 4,801,805 | 1/1989 | Butler et al. | 250/343 |
| 4,882,492 | 11/1989 | Schlager | 250/346 |
| 4,883,953 | 11/1989 | Koashi et al. | 250/226 |

FOREIGN PATENT DOCUMENTS 0160768 11/1985 European Pat. Off. .
0317121 5/1989 European Pat. Off. .

OTHER PUBLICATIONS

Peuchant et al., "Determination of Serum Cholesterol by Near-Infrared Reflectance Spectrometry", Anal. Chem., 1987, 59, 1816–1819.
Zeller et al., "Blood Glucose Measurement by Infrared Spectrometry", The International Journal of Artificial Organs, vol. 12/No. 2, 1989, pp. 129–135.
Bauer et al., Analytica Chimica Acta 197 (1987), pp. 295–301.
Lindberg et al., Analytical Chemistry, vol. LV, p. 643 (1983) article entitled "Partial Least-Squares Method for Spectrofluorometric Analysis of Mixtures of Humic Acid and Ligninsulfonate".
Martens et al., Applied Spectroscopy, vol. XL, p. 303 (1986) entitled "Near-Infrared Reflectance Determination of Sensory Quality of Peas".
Haaland et al., Analytical Chemistry, vol. XL, p. 1193 (1988) entitled "Partial Least Squares for Spectral Analyses" 1. Relation to Other Quantitative Calibration Methods and the Extraction of Qualitative Information.
Haaland et al., Analytical Chemistry, vol. LX, p. 1203 (1988) entitled "Partial Least-Squares Methods for Spectral Analyses. 2. Application to Simulated and Glass Spectral Data".
Haaland et al., Analytical Chemistry, vol. LX, p. 1208 (1988) entitled "Quantitative Infrared Analysis of Brophosphosilicate Films Using Multivariate Statistical Methods".
Haaland et al., Proceedings of Pittsburgh Conference, vol. XL, p. 874 (1989) entitled "Outlier Detection During Multivariate Quantitative Analysis of Spectroscopic Data".

Primary Examiner—Constantine Hannaher
Attorney, Agent, or Firm—Lowe, Price, LeBlanc, Becker & Shur

[57] ABSTRACT

The characteristics of a biological fluid sample having an analyte are determined from a model constructed from plural known biological fluid samples. The model is a function of the concentration of materials in the known fluid samples as a function of absorption of wideband infrared energy. The wideband infrared energy is coupled to the analyte containing sample so there is differential absorption of the infrared energy as a function of the wavelength of the wideband infrared energy incident on the analyte containing sample. The differential absorption causes intensity variations of the infrared energy incident on the analyte containing sample as a function of sample wavelength of the energy, and concentration of the unknown analyte is determined from the thus-derived intensity variations of the infrared energy as a function of wavelength from the model absorption versus wavelength function.

71 Claims, 8 Drawing Sheets

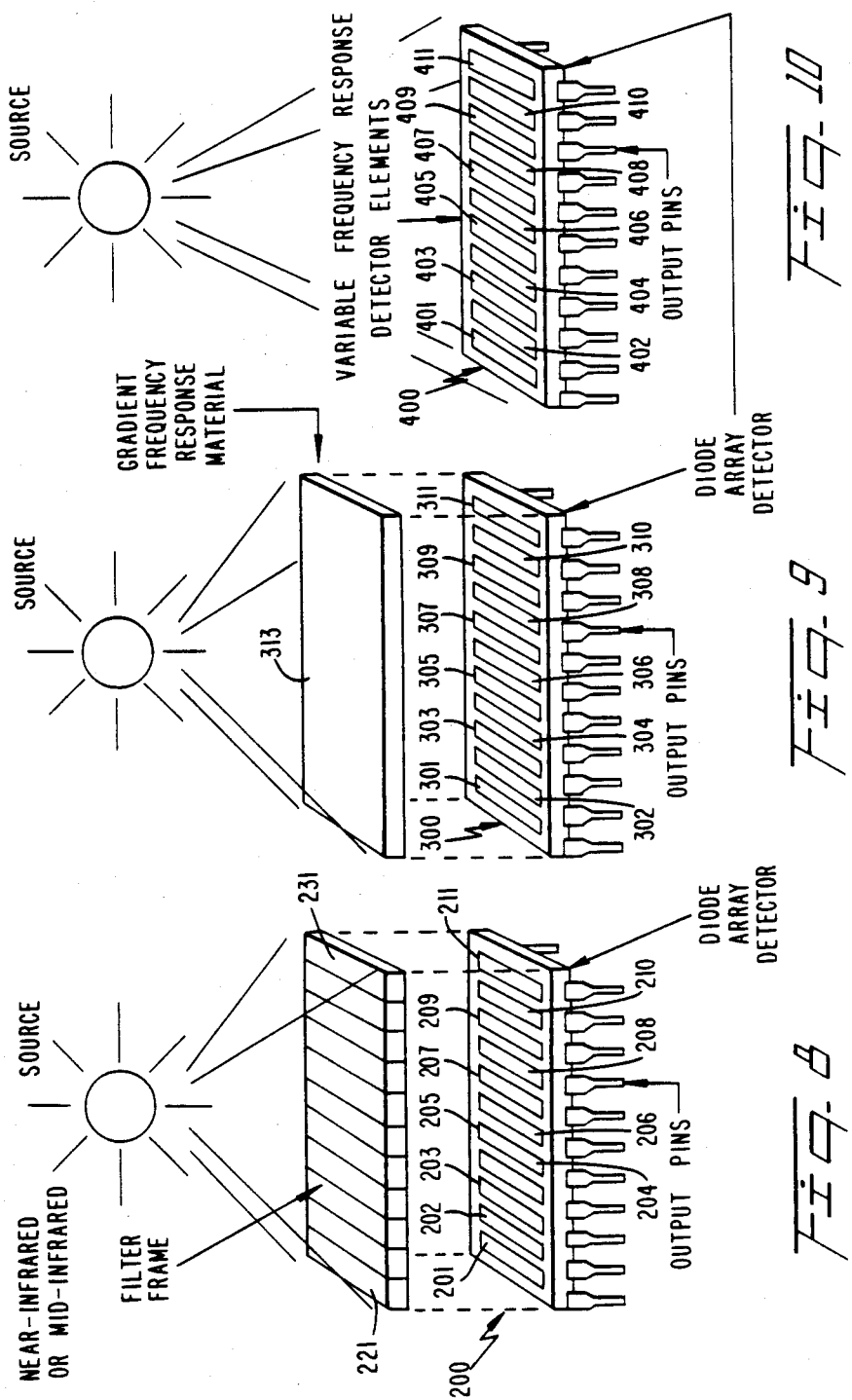

METHOD OF AND APPARATUS FOR DETERMINING THE SIMILARITY OF A BIOLOGICAL ANALYTE FROM A MODEL CONSTRUCTED FROM KNOWN BIOLOGICAL FLUIDS

FIELD OF THE INVENTION

The present invention relates generally to determining the nature, i.e., the similarity or concentration, of a biological analyte in comparison with a model constructed from plural known biological fluids, and, more particularly, to such a method and apparatus wherein a sample of biological fluid containing the analyte is irradiated with infrared energy having at least several wavelengths to cause differential absorption by the analyte as a function of the wavelengths and properties of the analyte.

BACKGROUND ART

For various care and treatment of mammal patients, it is necessary to determine concentrations of certain species in biological fluids. For instance, diabetics must be apprised of their blood glucose concentrations to enable insulin dosage to be adjusted. To determine blood glucose concentrations, blood is presently drawn several times per day by the diabetic, usually via a finger prick. If the blood glucose concentrations in such individuals are not properly maintained, the individuals become susceptible to numerous physiological problems, such as blindness, circulatory disorders, coronary artery disease, and renal failure. For these reasons, a substantial improvement in the quality of life of persons suffering from various maladies, such as diabetes mellitus, could be attained if the concentrations of species in body fluids are non-invasively and/or continuously determined. For example, for diabetic patients having external or implantable insulin pumps, a feedback loop for these pumps could be controlled by continuously monitoring glucose concentrations, to enable an artificial pancreas to be developed.

Exemplary systems have been previously proposed to monitor glucose in blood, as is necessary, for example, to control diabetic patients. This prior art is represented, for example, by Kaiser, U.S. Pat. No. 4,169,676, Muller, U.S. Pat. No. 4,427,889, and Dahne et al, European Patent Publication No. 0 160 768, and Bauer et al, *Analytica Chimica Acta* 197 (1987) pp. 295–301.

In Kaiser, glucose in blood is determined by irradiating a sample of the blood with a carbon dioxide laser source emitting a coherent beam, at a single frequency, in the mid-infrared region. An infrared beam derived from the laser source is coupled to the sample by way of an attenuated total reflectance crystal for the purpose of contacting the blood sample. The apparatus uses double beam instrumentation to examine the difference in absorption at the single frequency in the presence and absence of a sample. The reliability of the Kaiser device is materially impaired in certain situations because of the reliance on a single frequency beam for reasons explained below. Also, we have found from calculations based on available information that Kaiser's statement anent optical energy penetrating the skin to the depth of the blood capillaries is unlikely due to water absorption of the mid-infrared beam.

Muller discloses a system for quantifying glucose in blood by irradiating a sample of the blood with energy in a single beam from a laser operating at two frequencies in the mid-infrared region. The infrared radiation is either transmitted directly to the sample or by way of an attenuated total reflectance crystal for in vitro sampling. One frequency that irradiates the sample is in the 10.53–10.65 micrometer range, while the other irradiating frequency is in the 9.13–9.17 micrometer range. The radiation at the first frequency establishes a baseline absorption by the sample, while glucose absorption by the sample is determined from the intensity reduction caused by the sample at the second wavelength. The absorption ratio by the sample at the first and second frequencies quantifies the glucose of the sample. There is no glucose absorption at the first wavelength.

Dahne et al employs near-infrared spectroscopy for non-invasively transmitting optical energy in the near-infrared spectrum through a finger or earlobe of a subject. Also discussed is the use of near-infrared energy diffusely reflected from deep within the tissue. Responses are derived at two different wavelengths to quantify glucose in the subject. One of the wavelengths is used to determine background absorption, while the other wavelength is used to determine glucose absorption. The ratio of the derived intensity at the two different wavelengths determines the quantity of glucose in the analyte biological fluid sample.

Bauer et al discloses monitoring glucose through the use of Fourier-transform infrared spectrometry wherein several absorbance versus wavelength curves are illustrated. A glucose concentration versus absorbance calibration curve, discussed in the last paragraph on p. 298, is constructed from several samples having known concentrations, in response to the intensity of the infrared energy absorbed by the samples at one wavelength, indicated as preferably 1035 $cm^{-1}$.

All of the foregoing prior art techniques thus use only a single frequency analysis or ratio of two frequencies to determine a single proportionality constant describing a relationship between absorption of the infrared energy by the sample and concentration of a constituent of the biological fluid sample being analyzed, usually glucose. Hence, the prior art analysis is univariate since absorption by the constituent of interest at a single wavelength is determined.

However, univariate analysis has a tendency to be inaccurate in situations wherein there are concentration variations of any substance which absorbs at the analysis frequency. Biological systems are subject to numerous physiological perturbations over time and from person to person. The perturbations cause inaccuracies in univariate analysis, thereby decreasing the accuracy and precision of such analysis. The physiological perturbations involving any substance which absorbs at the analysis frequencies do not permit an operator of a system utilizing univariate analysis to recognize the resulting inaccuracy. In addition, nonlinearities may arise from spectroscopic instrumentation, refractive index dispersion, or interactions between molecules of the sample which cannot generally be modelled by univariate techniques. In addition, unknown biological materials in the sample have a tendency to interfere with the analysis process, particularly when these materials are present in varying amounts. Also the univariate techniques are usually not capable of identifying outlier samples, i.e., samples with data or constituents or spectra among the calibration or unknown data which differ from the remainder of the calibration set.

The described prior art systems utilizing midinfrared energy are not feasible for non-invasive in vivo determinations of glucose concentrations because of penetration depth limitations.

The most frequently employed prior art techniques for determining the concentration of molecular substances in biological fluids have used enzymatic, chemical and/or immunological methods. However, all of these techniques require invasive methods to draw a blood sample from a subject; typically, blood must be drawn several times a day by a finger prick, such as presently employed by a diabetic. For example, in the determination of glucose by diabetics, such invasive techniques must be performed using present technology. It would be highly desirable to provide a lessinvasive, continuous or semi-continuous system for automatically analyzing glucose concentrations in the control of diabetes mellitus.

It is, accordingly, an object of the present invention to provide a new and improved method of and apparatus for determining characteristics of a biological analyte sample.

Another object of the present invention is to provide a new and improved apparatus for and method of using infrared energy for analyzing biological fluids wherein the apparatus and method are particularly suitable for analyzing samples having concentrations of substances which variably or differentially absorb the infrared energy.

Another object of the invention is to provide a new and improved method of and apparatus for utilizing infrared energy to determine a characteristic, e.g., concentration, of a biological analyte by comparison of the absorption characteristics of said sample with a mathematical model constructed from several spectra of biological fluids having known absorption versus wavelength characteristics at known analyte concentrations.

A further object of the invention is to provide a new and improved apparatus for and method of analyzing biological fluids with infrared energy wherein interference with the infrared energy due to numerous physiological perturbations over time and between people does not have a particularly adverse effect on the results.

An additional object of the invention is to provide a new and improved apparatus for and method of using infrared energy to analyze biological fluids, wherein non-linearities due to various causes, for example, spectroscopic instrumentation, refractive index dispersion, and/or inter-molecular interactions, do not have an adverse effect on the analysis results.

An additional object of the present invention is to provide a new and improved apparatus for and method of using infrared energy to determine the nature of a biological sample wherein the presence of unknown biological materials in the sample does not interfere with the analysis of the sample, as long as these unknown biological materials are present in a calibration set which is used to derive a mathematical model which represents the response of known fluids to the infrared energy.

A further object of the invention is to provide a new and improved apparatus for and method of using infrared energy to determine characteristics of biological fluids wherein outlier samples subsisting in a calibration set used to derive a mathematical model are identified and either eliminated or accommodated so as not to have an adverse effect on the determination.

Another object of the invention is to provide a method of and apparatus for identifying the presence of outliers. The quality of the calibration results and the reliability of the unknown sample analyses can be critically dependent on the detection of outlier samples. In the calibration set, an outlier is a sample that does not exhibit the characteristic relationship between composition and the absorbance spectrum of the other calibration samples. During prediction, an outlier is a sample that is not representative of samples in the calibration set. Outliers in the calibration samples can impair the precision and accuracy of the calibration and limit the quality of the analyses of all future samples. The results of the analyses of outlier unknown samples by multivariate calibration cannot be considered reliable, and samples containing outliers should be analyzed by other methods. Thus, efficient detection of outlier samples is crucial for the successful application and wide acceptance of multivariate spectral analyses. For example, outliers occur as a result of changes in instrumental response, incorrect analyte determination by the reference method, unique type of sample, unexpected components, unusual baseline, incorrectly labeled or documented sample, etc.

Still an additional object of the invention is to provide a new and improved biological fluid analysis apparatus and method which is particularly adaptable, in certain embodiments, to non-invasive determinations.

THE INVENTION

In accordance with one aspect of the present invention, the concentration of a biological fluid containing an analyte is determined from a model constructed from plural known biological fluid samples. The model is a function of the concentration of materials in the known samples as a function of absorption at at least several wavelengths of infrared energy. The infrared energy is coupled to the analyte containing sample so there is differing absorption of the infrared energy as a function of the several wavelengths and characteristics of the analyte containing sample. The differing absorption causes intensity variations of the infrared energy passing through the analyte containing sample as a function of the several wavelengths. The thus-derived intensity variations of the infrared energy as a function of the several wavelengths are compared with the calibration model relating concentration to plural absorption versus wavelength patterns derived from the plural known biological fluid samples having various concentrations. The comparison enables the determination of the analyte concentration from the measured intensity variations for the biological fluid containing the analyte. In the preferred embodiment, the comparison is made in a computer by the partial least squares method, although other multivariate techniques can be employed.

In the computer implementation, the intensity variations as a function of wavelength are converted into plural first electric signals, such that different ones of the first electric signals are assigned to different ones of the wavelengths. The magnitude of each of the different first signals is determined by the intensity of the transmitted energy at the wavelength assigned to that particular first signal. The transmitted energy in the presence of the analyte containing sample is statistically compared with the transmitted energy in the absence of the sample to determine the absorption by the biological analyte containing fluid.

A multivariate statistical method, preferably using the partial least squares technique in a manner known in the statistical art, enables a model to be constructed of the infrared absorption versus wavelength characteristics and analyte concentrations. Following determination of the calibration model, the infrared absorption versus wavelength of the unknown fluid enables estimation of the analyte concentration. For example, if blood is being monitored, the glucose concentration of the blood can be determined by a statistical comparison between the model and the unknown sample absorption of the infrared energy at several wavelengths. If the absorption versus wavelength characteristics, i.e., spectrum, of the unknown fluid containing the analyte differ sufficiently from the spectrum generated by the model, the statistical analysis enables a determination to be made that the absorption of the unknown fluid at the different wavelengths does not closely enough match the model to provide any meaningful data. This is particularly important for certain applications, e.g., relating to insulin control for a subject. A controller for insulin injection is not activated in response to the absorption versus wavelength characteristics derived from the analyte if the analyte data do not adequately fit the model.

It has been found that the presence of alcohol in the blood of a diabetic overlaps with the analyte absorption versus wavelength characteristics to such an extent that accurate determination of glucose concentration is impossible with univariate methods, as in the prior art. By utilizing the multivariate technique of the present invention, it is possible to derive an indication that the absorption data for the unknown sample at several frequencies do not provide a basis upon which to derive meaningful glucose concentrations for determination of control signals to an insulin pump. Thereby, if the measured unknown spectrum differs to such an extent from the model that there is, in fact, no adequate fit between them, the insulin pump controller is not modified and the operator is made aware of a possible error in the concentration determination. If the partial least squares method is used to determine the fit between the model and the unknown sample absorption versus wavelength response, a statistical measure representing the quality of the fit between the model and the unknown spectrum in excess of a predetermined value provides an indication that analysis may be unreliable.

In accordance with a further aspect of the invention, outlier samples can be detected and/or eliminated from a calibration set of biological fluids. The outlier samples are detected and eliminated from the calibration set by utilizing the multivariate technique for each calibration sample forming the model. The absorption versus wavelength responses for at least several wavelengths of each of the fluids forming the calibration set are derived. The absorption versus wavelength characteristic of each sample is compared to the model generated from all of the other calibration samples. A predetermined level of acceptable variation for each sample spectrum from the model is established. A statistical test (typically the calculation of F-statistics or the Mahalanobis distance) is employed to determine which sample or samples of the calibration set exceed the predetermined level of acceptable variation. Hence, for example, if a particular fluid contemplated for use in establishing the calibration set differs from the remaining samples in the set by a predetermined amount, that particular fluid is not used as a member of the calibration set.

The respective intensity variations can be converted into electric signals using several different frequency dispersive techniques including Fourier transform techniques. One possible realization utilizes an array of infrared-to-electrical transducers, one of which is provided for each of the wavelengths so that different ones of the transducers derive different ones of the electric signals. In one of the embodiments, the array includes multiple individual filters each having a passband for one of the wavelengths. The filters are positioned relative to the transducers so that the infrared energy passed through one of the filters is incident on a corresponding one of the transducers. In a second embodiment, the array includes a sheet of infrared gradient wavelength responsive material having areas positioned relative to the transducers so that the infrared energy passed through different areas of the sheet is incident on corresponding different transducers. In a third embodiment, each of the transducers has a different chemical composition or is doped to be responsive to a different one of the several wavelengths.

In one embodiment, particularly adapted for monitoring in vitro biological fluids, the infrared energy is coupled to the fluid via an attenuated total reflectance crystal and the infrared source is in the mid-infrared spectrum. It is also possible to use external mid-infrared sampling for biological fluids which are circulating outside of the body, such as blood components during dialysis. For in situ analysis, such a crystal is implanted in the body and has a bio-compatible coating saturated or in contact with body fluids.

In a second embodiment, a catheter including a fiber optic element is inserted into an artery of a subject. The end of the fiber optic element in the artery has a reflective end coating. Infrared energy, either in the near-infrared or in the mid-infrared spectrum, illuminates the opposite end of the fiber optic element. The portion of the fiber optic element in the artery functions in the same manner as an attenuated total reflectance crystal. In systems utilizing the attenuated total reflectance element and the fiber optic element, blood or other body fluids irradiated by the optical energy of the infrared source differentially absorb the different frequencies to enable the multivariate analysis to be performed.

In a third embodiment, an optical fiber element transmitting in either the mid-infrared or near-infrared spectrum is inserted into the body for analysis of interstitial or subdermal fluid. The portion of the fiber in contact with the interstitial fluid functions in the same manner as an attenuated total reflectance element. In the specifically disclosed embodiments, such techniques are used for fluid monitoring in an earlobe through the use of a fiber optic loop including a fiber optic element that pierces the earlobe and transmits the non-absorbed energy to a frequency dispersing array.

In other embodiments of the invention, optical energy in the near-infrared spectrum is directly transmitted through a body portion and an analysis of wavelength versus absorption over several wavelengths of the spectrum is performed. In the specifically disclosed embodiments, a digit, such as the index finger of a subject, or an artery, is irradiated with several wavelengths in the near-infrared spectrum.

In a further embodiment, a biological sample fluid in an internal organ, such as the brain or liver, is irradiated by several wavelengths in the near-infrared spectrum.

A source of the near-infrared energy is placed in close proximity to a body part, such as the head or abdomen, containing biological fluid. The sample fluid in the organ diffusely reflects the near-infrared wavelengths and intensity versus wavelength responses at several wavelengths are measured and used in with the derived mathematical model to derive the analyte concentration.

Hence, the sample being analyzed includes a component that absorbs the infrared energy at a plurality of the wavelengths to which the source-detector combination is sensitive so that the thus-derived intensity variations are determined by absorption by the component at the plural wavelengths. The plural pre-stored patterns represent absorption by the known fluids at these plural wavelengths. The concentration determination step involves comparing the intensity of the thus-derived intensity variations at the plural wavelengths with a mathematical model derived from the absorption intensities of the prestored patterns at these plural wavelengths. The component, in a preferred embodiment, consists of glucose. However, the device could be used for quantitizing alcohol, ketones, fatty acids, cholesterol, lipoproteins, triglycerides, white blood cells, albumin, blood urea nitrogen, creatinine, concurrent medications such as drugs, inorganic molecules such as phosphates, and any other infrared absorptive component present in a biological analyte fluid.

Other source/detector configurations are feasible, such as a single or multiple element detector in conjunction with a dispersive Hadamard spectrometer or a Fourier transform infrared spectrometer. In addition, a standard prism or grating assembly could be employed. In the disclosed embodiment, there is a frequency dispersing arrangement to provide a unique frequency or wavelength intensity indication at each array element or channel. The disclosed structures for frequency dispersal, however, are of particular value for the present application because they are relatively small dispersion/detector assemblies.

The mid-infrared spectrum is preferred in applications utilizing attenuated total reflectance crystals or fiber optic elements because the mid-infrared frequencies have a severely limited penetration depth into biological fluids. The penetration depth of the mid-infrared spectrum into biological fluids occurs primarily as a result of water absorption so that transmission methods are not usually feasible in the mid-infrared spectrum. Hence, for embodiments of the invention using transmissivity, rather than reflectance, techniques, the infrared source is preferably in the near-infrared spectrum.

Typically, absorptivities of biological fluids in the mid-infrared spectrum are about an order of magnitude more intense than in the near-infrared spectrum. This is because the spectral features in the near-infrared spectrum are overtones and combination bands of spectral features in the mid-infrared region. While attenuated total reflectance methods could be used with a near-infrared source, the decreased absorptivity of molecular species in the near-infrared spectrum decreases the precision of the analysis, without any benefits relative to using energy in the mid-infrared region. Hence, for embodiments of the invention using attenuated total reflectance, the infrared source is preferably in the mid-infrared spectrum.

Certain embodiments of the invention are particularly adapted to be used for in situ investigations, wherein a device is implanted in the body of a subject. The embodiment utilizing the mid-infrared spectrum and the bio-compatible attenuating total reflectance crystal, the embodiment which monitors blood flow through an artery and the embodiment which monitors interstitial or subdermal fluids are designed to be implanted in the human body cavity. Such devices are particularly adapted to provide continuous control signals to an insulin pump of a diabetic. The insulin pump responsive to a detector of the present invention replaces the physiological activities of the pancreas by simultaneously sensing glucose levels and providing proper insulin delivery.

The above and still further objects, features and advantages of the present invention will become apparent upon consideration of the following detailed description of a specific embodiment thereof, especially when taken in conjunction with the accompanying drawings.

BRIEF DESCRIPTION OF DRAWING

FIG. 8 is a schematic, perspective view of a first embodiment of the invention employing multiple individual filter elements for providing frequency dispersion;

FIG. 9 is a schematic, perspective view of a second embodiment of a frequency dispersion device wherein a single gradient response filter sheet controls the wavelength of infrared energy incident on elements of a diode array detector; and FIG. 10 is a perspective view of a further embodiment of the invention wherein each element of a diode detector array is constructed so that it is responsive to optical energy of a different infrared wavelength.

DESCRIPTION OF THE PREFERRED EMBODIMENTS

Figure 1:
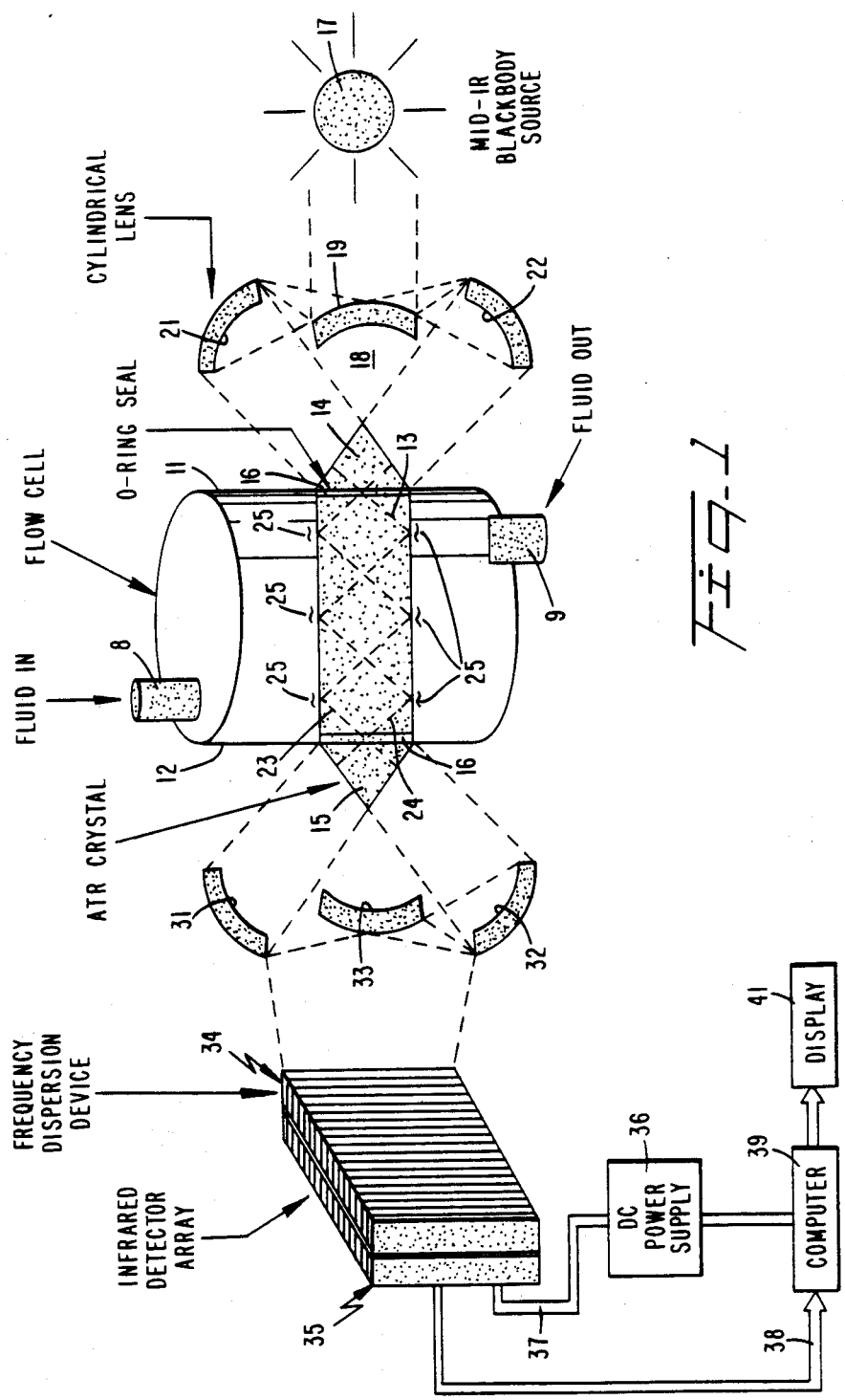
FIG. 1 is a schematic diagram of a first embodiment of the invention, particularly adapted for monitoring in vitro biological fluids using mid-infrared spectroscopy and an attenuated total reflectance crystal.

Reference is now made to FIG. 1 of the drawing wherein vessel 11 contains human blood sample 12 to be analyzed for glucose content. Blood analyte sample 12 is obtained from a typical in vitro source, such as from a patient undergoing surgery in a hospital operating room or a patient in a hospital intensive care ward. Blood analyte flows into and out of vessel 11 via conduits 8 and 9, respectively. Extending between and through end walls of vessel 11 is attenuated total reflectance crystal 13, having an index of refraction greater than the index of refraction of blood sample 12. Crystal 13 includes conical, opposite end portions 14 and 15 which extend beyond end walls of vessel 11. O-ring seals 16 secure crystal 13 in place in apertures of the end walls of vessel 11, to prevent leakage of analyte sample 12 from the vessel.

Optical energy from wideband mid-infrared (between 50 and 2.5 micrometers) black body source 17 is coupled to tapered wall portion 14 via lens assembly 18. Lens assembly 18 includes central convex reflector surface 19, having an axis coincident with the longitudinal axis of crystal 13. Convex surface 19 faces source 17, that is aligned with the axis of crystal 13. Lens assembly 18 comprises a circular mirror including concave reflecting surfaces 21 and 22, respectively positioned above and below the longitudinal axis of crystal 13. Concave reflecting surfaces 21 and 22 are disposed on opposite sides, above and below, reflecting surface 19. Reflecting surfaces 19, 21 and 22 are such that optical energy from source 17 is initially incident on reflecting surface 19, thence is reflected to concave reflecting surfaces 21 and 22 and thence is directed to conical end portion 14 of crystal 13. The optical energy from source 17 coupled to crystal 13 is reflected in the crystal as shown by ray paths 23 and 24. The structure illustrated in FIG. 1 including vessel 11, crystal 13 and lens assembly 18 is commercially available from Spectra-Tech, Inc., under the CIRCLE CELL trademark.

Some of the optical energy coupled from source 17 to crystal is transmitted from the crystal to sample 12, as shown by wavy lines 25 just beyond the intersection of the crystal and sample. Different wavelengths, i.e., frequencies, of source 17 are differentially absorbed by sample 12 as a function of concentrations of organic and inorganic molecules in the sample. In other words, certain wavelengths emitted by source 17 are absorbed by sample 12 to a greater extent than other wavelengths from the source. The absorption occurs in sample 12 just beyond the interface between crystal 13 and the sample. Since the degree of absorption determines the amount of reflectance, those wavelengths which are most highly absorbed have the lowest intensity as they propagate from tapered, conical end portion 15 of crystal 13.

The intensity versus wavelength characteristics of the infrared energy for at least several of the wavelengths of source 17 propagated from end portion 15 of crystal 13 are detected to enable the concentration of sample 12 to be determined. To this end, the infrared energy propagating from conical end face portion 15 of crystal 13 is incident on concave reflecting surfaces 31 and 32. From reflecting surfaces 31 and 32, the non-absorbed infrared energy from source 17 is incident on the convex reflecting surface 33. From reflecting face 33, the optical energy is coupled to a frequency dispersion device 34 including diode array detector 35.

Frequency dispersion device 34 and photodiode array detector 35 are arranged so that the array includes multiple output leads, one of which is assigned to a particular wavelength or narrow range of wavelengths of source 17. The amplitude of the voltage developed on each of the leads is commensurate with the intensity of the infrared energy incident on each particular detector in array 35 for the wavelength of the source associated with that detector. Typically, the photodiodes of array detector 35 are passive, rather than photovoltaic although photovoltaic devices may be employed. Thereby, the diodes of array detector 35 must be supplied with DC power supply voltages, as derived from power supply 36 and coupled to the diodes of array detector 35 via cable 37. The impedance of the diode elements of array detector is changed as a function of the intensity of the optical energy incident thereon in the passband of source 17 associated with each particular photodiode element. The impedance changes control the amplitude of signals supplied by array detector 35 via bus 38 to a random access memory of computer 39.

Computer 39 includes a memory having stored therein a multivariate statistical model determined from the concentration versus absorbance versus wavelength characteristics of several known blood samples. Such a model is constructed using techniques known by statisticians.

Computer 39 determines the biological characteristics of analyte sample 12 by comparing the model with the amplitude versus wavelength response from array 35. Preferably, the comparison is made by a partial least squares technique, as disclosed, for example, by Lindberg et al, *Analytical Chemistry*, Vol. LV, p. 643 (1983) in an article entitled, "Partial Least-Squares Method for Spectrofluorometric Analysis of Mixtures of Humic Acid and Ligninsulfonate;" Martens et al, *Applied Spectroscopy*, Vol. XL, p. 303 (1986) entitled "Near-Infrared Reflectance Determination of Sensory Quality of Peas;" Haaland et al, *Analytical Chemistry*, Vol. LX, p. 1193 (1988) in an article entitled "Partial Least Squares for Spectral Analyses. 1. Relation to Other Quantitative Calibration Methods and the Extraction of Qualitative Information;" Haaland et al, *Analytical Chemistry*, Vol. LX, p. 1203 (1988) in an article entitled "Partial Least-Squares Methods for Spectral Analyses. 2. Application to Simulated and Glass Spectral Data;" Haaland, *Analytical Chemistry*, Vol. LX, p. 1208 (1988), in an article entitled "Quantitative Infrared Analysis of Brophosphosilicate Films Using Multivariate Statistical Methods;" and Haaland et al, *Proceedings of Pittsburgh Conference*, Vol. XL, p. 874 (1989) in an article entitled "Outlier Detection During Multivariate Quantitative Analysis of Spectroscopic Data." While the partial least squares method has been found to be precise, other techniques, such as a principal component regression analysis, can be utilized to determine the greatest similarity between the mathematical model and the amplitude versus wavelength response resulting from the unknown, tested fluid.

Considerable improvement in detection precision is obtained by simultaneously utilizing at least several wavelengths from the entire spectral frequency range of source 17 to derive data for a multivariate analysis. The multivariate method allows both detection and compensation for interferences, the detection of outlier samples, as well as for modelling many types of non-linearities. Since the calibration samples used to derive the model have been analyzed on a multivariate basis, the presence of unknown biological materials in sample 12 does not prevent or distort the analysis. This is because these unknown biological materials are present in the prestored multivariate calibration samples used to form the model. The multivariate method provides for detection of outliers, i.e., those samples that do not exhibit the characteristic relationship between composition and the absorbance spectrum of other calibration samples. Identifying and removing outlier samples from the calibration set improves the accuracy and precision of the analysis. Identification of the spectrum of sample 12 as an outlier (dissimilar from the calibration set) provides methods of evaluating the validity of the concentration prediction calculations. Identification of an outlier spectrum from unknown samples, such as sample 12, is important since the results from analysis of an outlier sample are unreliable. Dire consequences could result if clinical decisions were to be based on unreliable analyses. It is also possible, utilizing known statistical methods, to identify the reason a sample is an outlier from the multivariate analysis, such as a malfunctioning apparatus.

After the partial least squares technique has been employed by computer 39 to determine the characteristics of sample 12, the computer derives an indication of the concentration of the analyte in the unknown sample. For example, the computer derives the concentration of glucose in the bloodstream. The indication derived by computer 39 is coupled to conventional alphanumeric visual display 41.

The device illustrated in FIG. 1 is used to examine in vitro drawn samples as obtained from blood routed outside the body. A similar structure could also be used to analyze urine, saliva and other biological fluids for infrared active analytes thereof.

Figure 2:
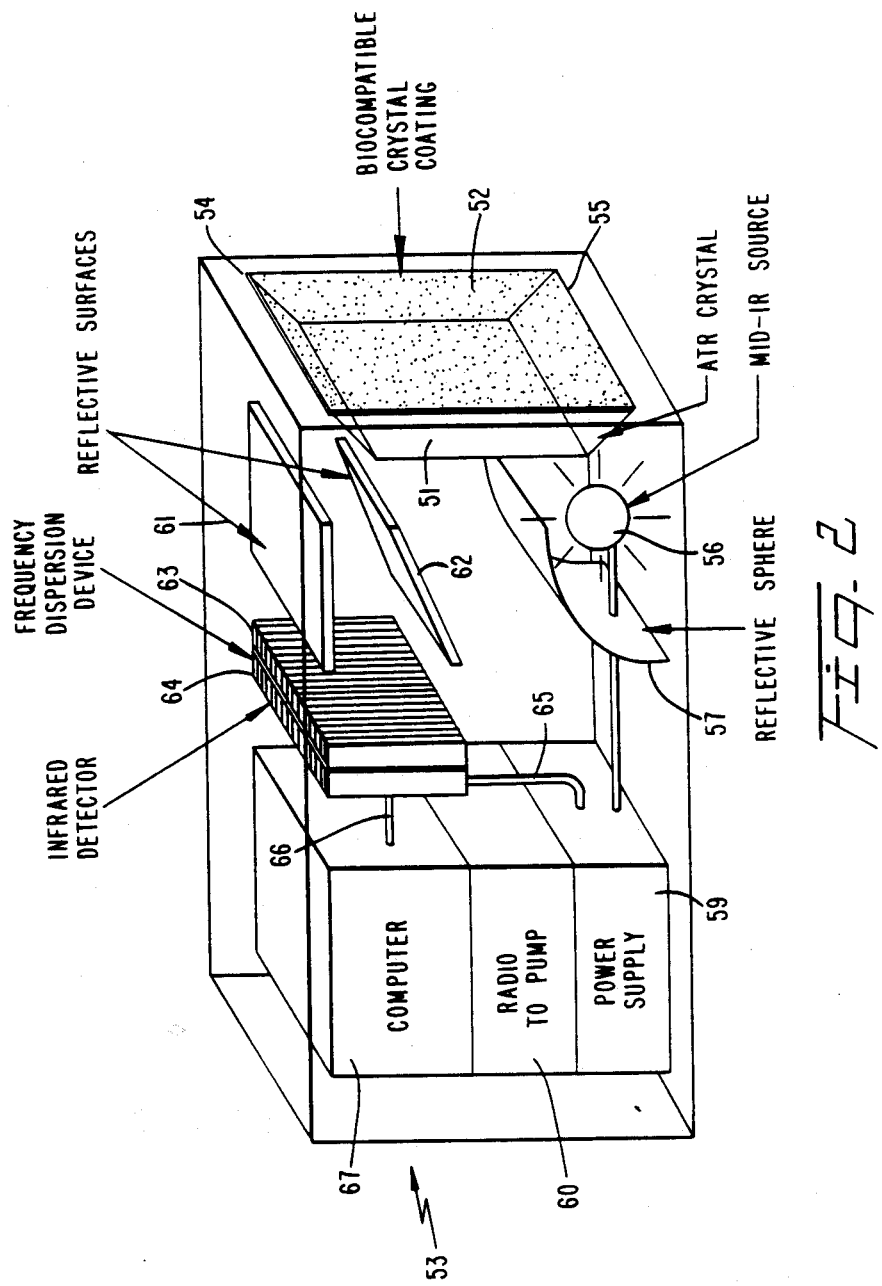
FIG. 2 is a schematic diagram of another embodiment of the invention employing an implanted sensor for monitoring biological fluids using mid-infrared spectroscopy and an attenuated total reflectance crystal.

A device operating on principles similar to those of the device illustrated in FIG. 1, but which is implantable in the human body, is illustrated in FIG. 2. The device illustrated in FIG. 2 includes attenuated total reflectance crystal 51 having a planar face with biocompatible crystal coating 52 thereon. Coating 52, fabricated from any suitable material, such as a polyurethane foam, is in direct contact with the biological fluids of interest. Coating 52 is a porous film permitting penetration of molecular species smaller than antibodies so that the molecular species of the blood or other biological fluid is in direct contact with the face of crystal 51. Alternatively, coating 52 could be thin enough to permit penetration of infrared optical energy from crystal 51 directly into body fluid or tissue.

Crystal 51 includes inclined end faces 54 and 55 between which coating 52 extends. End face 54 transmits optical energy from mid-infrared source 56, located in housing 53 and surrounded by reflector 57, having a circular cross section and shaped as a sheet. Reflector 57 includes end face 55, adjacent mid-infrared source 56, so that infrared energy from source 56 is coupled to end face 55 and to the crystal interior. Infrared source 56 is energized by DC power supply 59 in housing 53.

The biological body fluid in contact with coating 52 differentially absorbs the several wavelengths of wide band source 56. Thereby, the infrared energy at the different wavelengths of source 56 has variable intensity as it is propagated from end face 55 of crystal 51. The infrared energy propagating from end face 55 is generally directed in an upward manner, to be incident on horizontally extending reflective surface 61 and inclined reflective surface 62.

The wide band infrared energy incident on reflective surfaces 61 and 62 is directed to frequency dispersion device 63, thence to diode array detector 64, energized by power supply 59 via bus 65. Detector array 64 includes multiple output leads in bus 66 so that the amplitude of the signal on each lead in bus 66 represents the intensity of the infrared energy associated with a particular passband associated with each detector element of the array. The signals in bus 66 are coupled to a random access memory of computer 67 which is constructed in the same manner as computer 39, FIG. 1. After computer 67 determines the characteristics of analyte fluid contacting coating 52 from the intensity versus wavelength variations incident on array 64, the computer activates an insulin pump to control the glucose concentration of the subject. Alternatively, the data on bus 66 could be transmitted to a computer external to the body of the subject. A wireless communication link for control of the pump or for the data is established by radio transmitter 60, connected to computer 67 or bus 66, as required.

Figure 3:
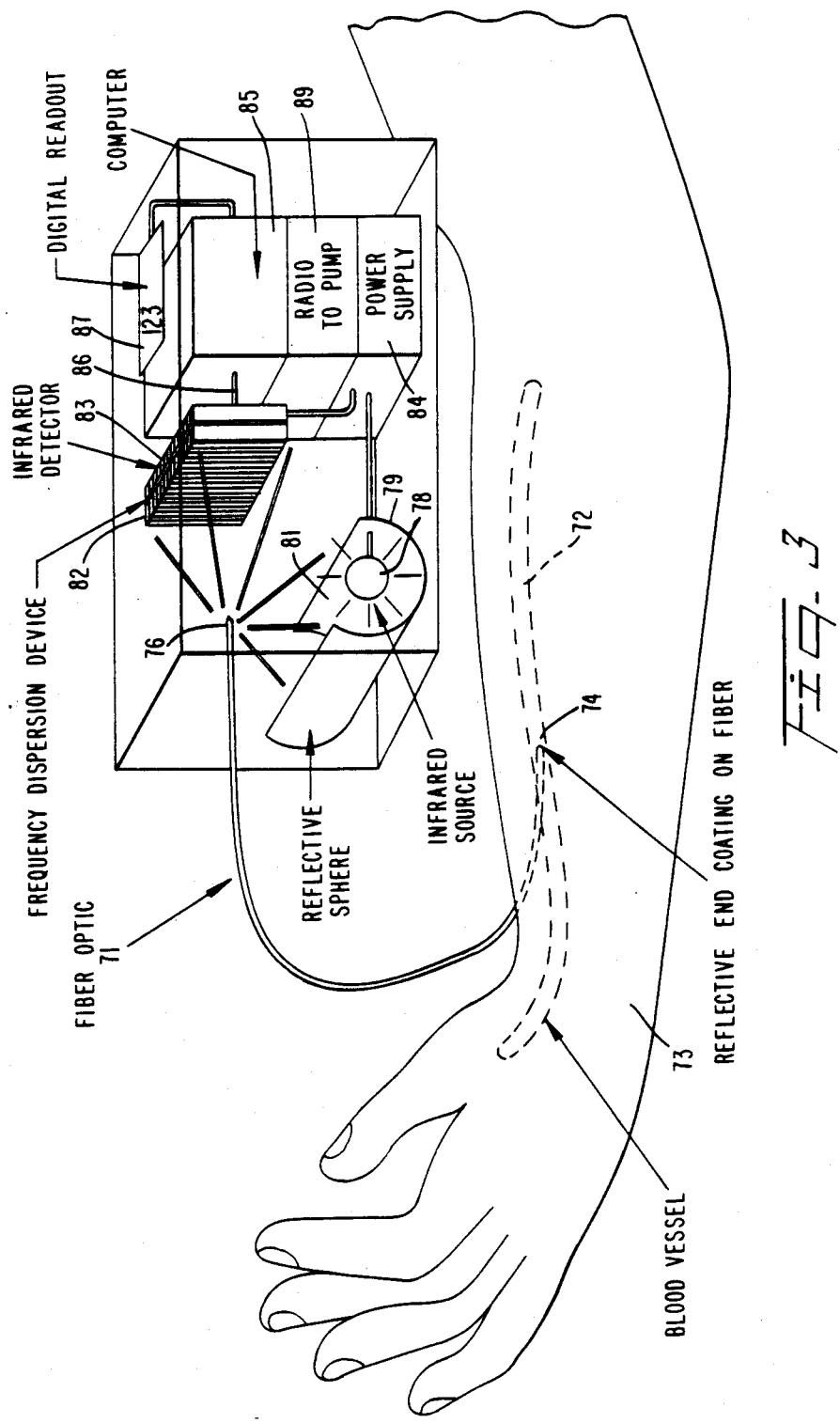
FIG. 3 is a schematic diagram of a further embodiment of the invention wherein blood in an artery is sampled via a fiber optic element for a mid-infrared or a near-infrared source.

Reference is now made to FIG. 3 of the drawing wherein fiber optic element 71, surrounded by a catheter (not shown) is illustrated as being inserted into artery 72 of arm 73 of a subject. Fiber optic element 71 is a single fiber optic infrared transmitter having an infrared reflective coating for internal reflection, as well known in the art. The end of fiber optic element 71 positioned in artery 72 includes reflective end face coating 74, while the opposite end of the fiber optic element in housing 75 has conical tip 76.

One side of conical tip 76 is illuminated by wide band infrared energy either in the mid-infrared range or near-infrared (2.5–0.7 micrometers) range, as derived from a source including infrared emitter 78 and reflector 79 having a circular sheet-like reflecting surface. Reflector 79 includes opening 81 in proximity to one side of conical end 76. Optical energy from source 78 incident on one side of conical tip 76 is transmitted from the tip along the length of fiber optic element 71 to artery 72. The optical energy in fiber optic element 71 is reflected from end face 74 back along the length of the fiber optic element to conical tip 76. The portion of fiber optic element 71 imbedded in artery 72 does not include the usual protective coating such as a polyamide coating. Since the index of refraction of fiber optic element 71 is greater than that of the blood in artery 72 the fiber optic element functions along the entire length embedded in the artery basically in the same manner as attenuated total reflectance crystals 13 and 51.

The infrared optical energy transmitted back from artery 72 via fiber optic element 71 to conical tip 76 is transmitted from the side of the conical tip opposite from the side adjacent opening 81 so that the energy transmitted from the tip is incident on frequency dispersion device 82, thence is coupled to diode detector array 83. Detector array 83 and infrared source 78 are energized by DC power supply 84. Detector array 83 supplies computer 85 with signals via bus 86 to indicate the infrared absorption by the blood in artery 72 of the optical energy from source 78 for each of several frequency bands of the source. Computer 85 includes a program with a read only memory as described supra with regard to computer 39, to determine the characteristics of the blood in artery 72.

The optical energy from tip 76 is coupled to frequency dispersion device 82 via a reflective system (not shown) somewhat similar to that illustrated in FIG. 2. Such a reflective system is desirable because the emitting surface of conical tip 76 is off axis from frequency dispersion device 82 and diode detector array 83.

Fiber 71 has several advantages, relating to flexibility, ability to transmit light to remote locations and small diameter, usually less than a millimeter, to provide intravascular, intramuscular, interstitial and transdermal use. With the currently available fiber optic elements, source 78 may be either a mid-infrared or a near-infrared wideband emitter. Currently available fiber optic elements are more transmissive in the 2.5–0.7 micrometer, near-infrared region than in the mid-infrared 50–2.5 micrometer region. However, the near-infrared region has the disadvantage of relatively low absorptivity by organic species relative to the absorptivity in the mid-infrared region.

The device of FIG. 3 could also be an interstitially imbedded optical fiber system or could be used to measure concentrations of biological fluid analytes outside of the vascular system.

In response to the comparison made by computer 85 of the model stored therein with the data derived from bus 86, the computer derives an indication of the characteristics of the analyte fluid in artery 72. The comparison and resulting concentration computation are made in computer 85 by the partial least squares technique. The concentration indication is supplied by computer 85 to alphanumeric display 87.

The model stored in computer 85 is computed by a general purpose computer using the partial least squares method with absorption versus wavelength responses from plural known biological samples. The concentration in each of the known biological samples is typically determined using invasive enzymatic, chemical or immunological techniques. The model data relating absorption versus wavelength response to concentration are read from the general purpose computer into the memory of microcomputer 85 prior to installation of the microcomputer into the apparatus illustrated in FIG. 3. The partial least squares computation by computer 85 also enables a determination to be made that the absorption versus wavelength response for the measured unknown sample cannot be associated with the concentration of the analyte in the blood. In particular, if the F-statistic determined using the partial least squares algorithm and computed from the model and unknown sample absorption versus wavelength response exceeds a predetermined value, the analyte concentration in the unknown sample cannot be reliably determined. If this happens, display 87 is activated accordingly and no control such as via radio transmitter 89, over an insulin pump is instituted.

Figure 4:
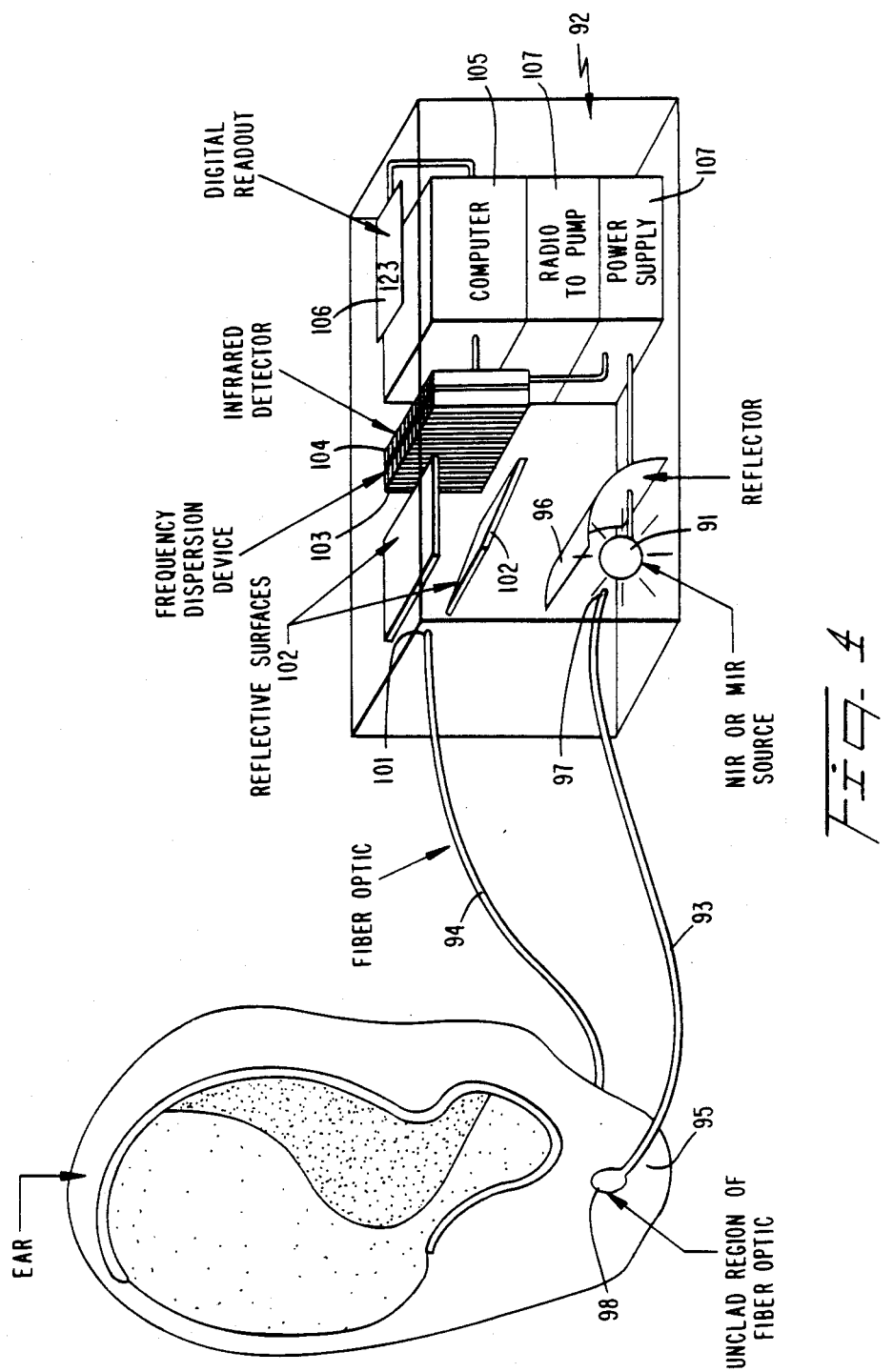
FIG. 4 is a schematic diagram of a further embodiment of the invention using a fiber optic loop for monitoring biological fluids in an earlobe of a subject, wherein the earlobe is irradiated via the fiber optic loop by a source emitting several wavelengths of optical energy in the near-infrared or mid-infrared spectrum.

In the embodiment illustrated in FIG. 4, several infrared wavelengths in the near-infrared or mid-infrared range are transmitted from wide band source 91 in housing 92 via a fiber optic loop including fiber optic element 93 to ear lobe 95 of a human subject. The protective coating of optical fiber element 93 is removed to allow contact of the fiber with the ear as the fiber pierces through a portion of the ear. The exposed portion of the fiber surrounded by the ear thereby acts as an attenuated total reflectance element. Following penetration of the ear, the optical fiber is again coated with a protective coating. The optical energy is transmitted from endface 97 to endface 101 by a continuous fiber with only region 98 extending through the earlobe being uncoated so there is an interaction of the infrared light transmitted through element 93 with the surrounding sample medium in the ear lobe.

The infrared energy emerging from end face 101 is transmitted by horizontal and inclined planar reflectors 102 to frequency disperser 103 and diode detector array 104. Frequency disperser 103 and diode detector array 104 function with computer 105, display 106 and power supply 107 in the same manner as described supra, with regard to FIGS. 1–3. A radio transmitter 108 may also be incorporated.

A fiber optic loop system similar to that of FIG. 4 can be used to penetrate other portions of the body which permit sampling of the subdermal region. These types of arrangements can also be used with an uncoated optical fiber in a disposable needle device. In such a situation, the fiber is changed daily to prevent fibrin accumulation on the needle. It has been found that such a disposable needle penetrating the body is very well suited to control insulin delivery for waist-mounted insulin pumps.

The fiber optic transmission system of FIG. 4 is more suitably used in conjunction with infrared sources in the near-infrared region than sources in the mid-infrared region. This is because the longer attenuation by currently available fiber optic elements for mid-infrared wavelengths than for near-infrared wavelengths. The devices illustrated in FIGS. 1–4 all use attenuated total reflectance principles. The invention is also applicable to techniques using transmission of infrared energy, usually in the near-infrared range.

Figure 5:
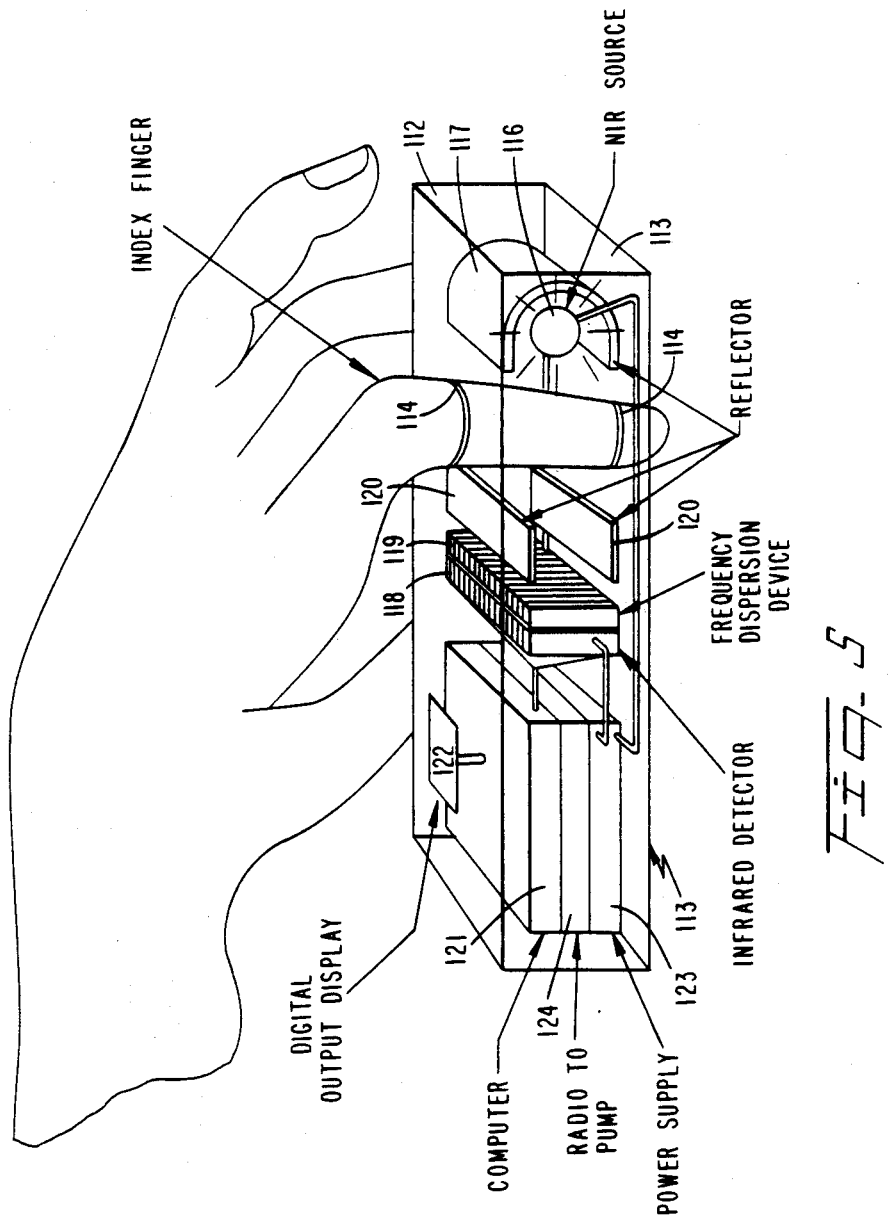
FIG. 5 is a schematic, perspective view of a further embodiment of the invention particularly adapted for monitoring blood components in a human index finger using near-infrared spectroscopy and non-invasive transmission sampling.

The present invention can be used to analyze biological fluids in other body parts. In the embodiment of FIG. 5, used to monitor blood in the index finger of a human subject, housing 111 includes parallel top and bottom faces 112 and 113, each having mating, aligned apertures 114, particularly adapted to receive a subject index finger. The volume in housing 111 between apertures 114 thus defines a cylinder, on opposite sides of which are located near-infrared source 116 and frequency dispersion device 119. Near-infrared source 116 is surrounded by sheet-like reflector 117 having a circular cross section. Optical energy from source 116 is transmitted directly toward frequency dispersion device 119 and is reflected by reflector 117 so that rays of the near-infrared energy are transmitted through an index finger inserted into housing 111. The rays transmitted through the finger are incident on frequency dispersion device 119 and on parallel horizontally disposed reflecting surfaces 120 which directs them to device 119. In close proximity to frequency dispersion device 119 is diode detector array 118 which supplies computer 121 with signals to enable display 122 to be energized. Power supply 123 energizes the diodes of array 118 and source 116. A radio transmitter 124 such as previously discussed may also be incorporated.

Hence, in the embodiment of FIG. 5, optical energy in the near-infrared spectrum is transmitted directly through the index finger inserted through apertures 114 into housing 111. Blood in the index finger differentially absorbs different wavelengths from source 116. The differential absorption is detected by monitoring the amplitude at the different wavelengths coupled by frequency dispersion device 119 to diode detector array 118.

Principles of the direct near-infrared transmission system illustrated in FIG. 5 can be used to measure concentrations of species in other body parts. For example, housing 111 can be modified so that the abdomen, ear lobe, wrist or other appendages are located between the near-infrared source and reflector combination and the frequency dispersion device and diode detector array.

Figure 6:
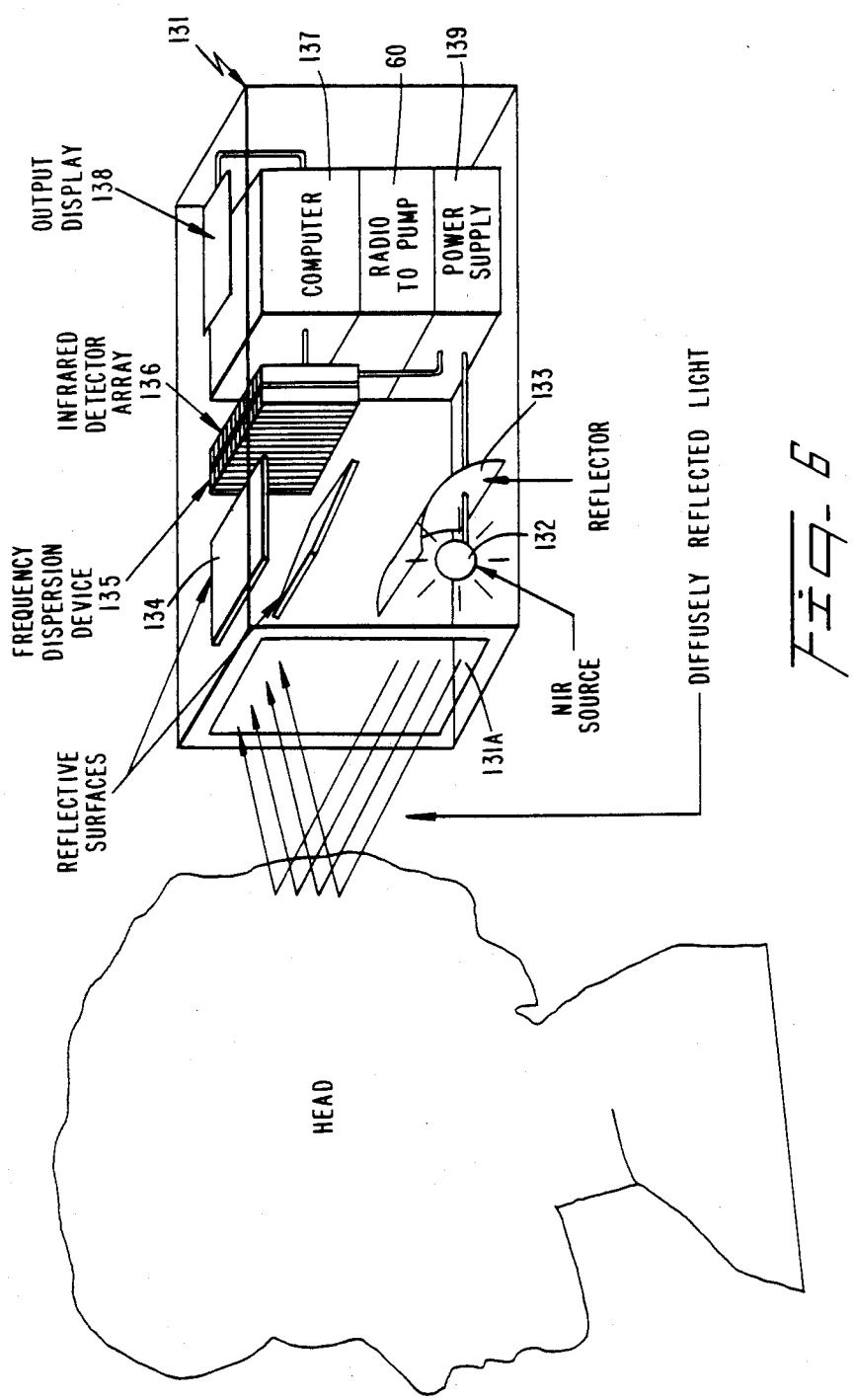
FIG. 6 is a schematic, perspective view of a further embodiment of the invention for monitoring biological fluids in the brain non-invasively by using near-infrared spectroscopy and diffuse reflectance sampling.

The device illustrated in FIG. 6, used to monitor biological fluids non-invasively using near-infrared spectroscopy and diffuse reflectance sampling, includes housing 131 in which are located near-infrared source 132 and reflector assemblies 133 and 134. Reflector assembly 133 is configured as a sheet having a cross section that is a segment of a circle and approximately surrounds source 132 and has an opening at one end face 131a of housing 131. Reflector assembly 134, located immediately above reflector assembly 133, includes an opening in the same end face of housing 131. The end face of housing 131 where the apertures of reflector assemblies 133 and 134 are located is adapted to be placed directly against a body part, such as the head or the abdomen, for monitoring biological fluids in the brain or liver. The optical energy from source 132 and reflector assembly 133 penetrates to the interior of the body part of interest and is diffusely reflected from the blood or other biological fluid in the organ being monitored. The optical energy from source 132 and reflector 133 is differentially absorbed by the organ being analyzed within the body, so that diffusely reflected optical energy propagated from the organ through the body is incident on reflector assembly 134. The diffusely reflected infrared energy incident on reflector assembly 134 is coupled to frequency dispersion device 135, thence to diode detector array 136 which drives computer 137 to energize display 138, as described supra. Power supply 139 energizes infrared source 132 and diode detector array 136. A radio transmitter 139a may also be used.

Figure 7:
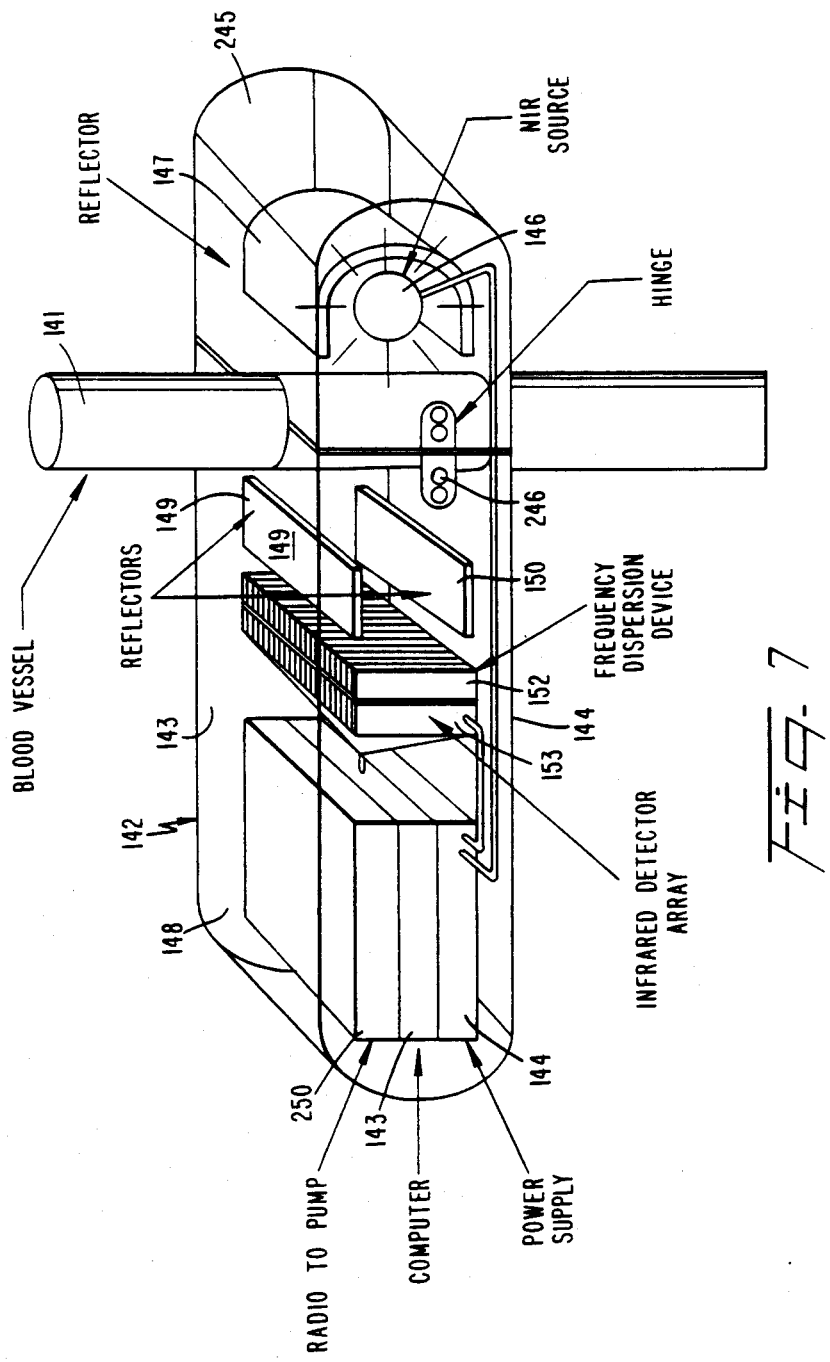
FIG. 7 is a schematic, perspective view of another embodiment of the invention wherein a body implanted housing containing a near-infrared source irradiates blood in an artery of a subject.

Reference is now made to FIG. 7 of the drawing, a schematic diagram of an implantable apparatus for monitoring biological fluids using near-infrared spectroscopy, wherein near-infrared energy is transmitted through an internal body part, such as artery 141. The apparatus illustrated in FIG. 7 is located in housing 142, including parallel top and bottom faces 143 and 144 having mating circular apertures such as 143a through which artery 141 is adapted to fit. Housing 142 includes hinged end portion 245, connected to the remaining, main portion 148 of the housing by hinge 246. Housing portions 245 and 148 include a latch arrangement (not shown) so that artery 141 can be surrounded by the housing and fit into the mating circular apertures.

End portion 245 of housing 142 includes near-infrared source 146, surrounded by sheet-like reflective element 147, having a cross section that is a segment of a circle. Main portion 148 of housing 142 includes parallel planar, horizontally disposed reflective elements 149 and 150 which direct optical energy transmitted from source 146 and reflector 147 through artery 141 onto frequency dispersion device 152. Frequency dispersion device 152 is located in the main part of housing 142 and is optically coupled to diode detector array 153 which supplies signals to computer 154 that communicates with an insulin pump via a wireless link including radio transmitter 250. Alternatively, the signals from diode detector array 153 are coupled to an external computer via the wireless link. Near-infrared source 146 and the diodes of detector array 153 are energized by DC power supply 155.

Devices similar to that illustrated in FIG. 7 could be used for transmission through other tissues, such as the liver, for examining bile, or the bladder for urine analysis. A further variation of the implanted device of FIG. 7 involves the use of an external near-infrared source, to conserve energy of the power supply. In such an instance, optical energy from the near-infrared source is transmitted through a tissue sample to an implanted detection apparatus. Infrared energy transmitted through the tissue is incident on a frequency dispersion device and a diode detector array.

Three preferred embodiments of the frequency dispersion device and the diode detector array of any of FIGS. 1-7 are illustrated in FIGS. 8-10. In each of the embodiments of FIGS. 8-10, infrared energy is incident on a passive elongated diode of the detector array. Each diode has associated therewith a certain wavelength range, either in the mid-infrared or near-infrared spectrum. The intensity of the infrared radiation incident on each semiconductor diode changes the charged carrier density of the diode to control the impedance thereof between the diode anode and cathode electrodes. Each diode is energized by a DC voltage from the power supplies of FIGS. 1-7, so that the voltage output of each diode varies as a function of the intensity of the incident infrared energy in the band of interest for the particular diode.

To these ends, diode detector array 200, FIG. 8, includes several elongated, mutually insulated semiconductor diodes 201-211, having mutual planar faces on which is superimposed filter frame 213 including an equal number of several individual elongated infrared filter elements 221-231. Each of filter elements 221-231 is superimposed on and abuts against a corresponding one of diodes 201-211. Each of elongated filters 221-231 has a bandpass for a different wavelength interval in the mid-infrared or near-infrared spectrum. Thereby, a voltage is derived across the electrodes of each of diodes 201-211, which voltage is indicative of the intensity of the radiation in the infrared region passed by the filter abutting against the particular diode. The signals across the electrodes of diodes 201-212 are supplied to a bus, such as bus 38, FIG. 1, which couples the signals to designated locations in the computer random access memory.

A similar result is obtained with the structure of FIG. 9, wherein diode detector array 300 is identical to array 200, FIG. 8, and thereby includes several parallel, elongated semi-conductor diode elements 301-311. Superimposed on the elongated planar faces of the diodes of array 300 is planar sheet 313, fabricated of a variable frequency response material. The material of sheet 313 is arranged so that the material in the sheet on one side (e.g., the left side thereof, as illustrated in FIG. 9), is transparent only to the shortest wavelength of interest in the near-infrared spectrum emitted by the near-infrared source or only the shortest wavelength of interest in the mid-infrared spectrum emitted by the mid-infrared source. At the right side of sheet 313, the material of the sheet is transparent only to the longest wavelengths of interest in the near-infrared or mid-infrared spectra of the source.

The intermediate portions of sheet 313 are fabricated of material that is transparent only to intermediate portions of the near-infrared or mid-infrared spectra. The bandpass of the material in sheet 313 progressively increase in wavelength from the left to the right edge of the sheet. Sheet 313 abuts against elements 301-311 of array 300 so that diode 301 is responsive basically to the same range of wavelengths as diode 201 in array 200 of FIG. 8. Similarly, elements 302-311 of array 300 derive responses for the same wavelengths as corresponding elements 202-211 of array 200.

Similar results are attained with the detector array of FIG. 10, wherein array 400 includes several elongated semiconductor detectors 401-411. Each of the diodes 401-412 is differentially doped so that it is responsive to a different wavelength in the near-infrared or mid-infrared spectrum. Hence, diode 401 is fabricated or doped so that it is responsive only to infrared energy having the shortest wavelength of interest in the near-infrared spectrum or in the mid-infrared spectrum. Diode 411 is doped so that it is responsive only to the longest wavelengths of interest in the near-infrared or mid-infrared spectra. Intermediate diodes 402-410 are fabricated or doped so that they are responsive to successively longer wavelengths in the near-infrared or mid-infrared spectra.

The multivariate approach of the present invention permits the concentration of molecular substances in fluids to be predicted without the use of enzymatic, chemical or immunological methods. The partial least squares technique produces results as precise as reactive determinations by the enzymatic, chemical or immunological methods. By using the multivariate mid-infrared and near-infrared techniques, it is possible with the invention to determine the concentrations of substances without penetrating the body, except for the optical radiation. Such a non-invasive determination has a well defined need in the control of diabetes mellitus. The invention has use for determining the levels of alcohol, ketones, fatty acids, cholesterol, lipoproteins, triglycerides, white blood cells, albumin, blood urea nitrogen, creatinine, concurrent medications, such as drugs, inorganic molecules such as phosphates, and detection of other infrared active compounds. The disclosed configurations can be continuously or intermittently operated to transmit concentration or dosage data to an implanted or external pump for drug delivery, such as for insulin.

While there have been described and illustrated several specific embodiments of the invention, it will be clear that variations in the details of the embodiments specifically illustrated and described may be made without departing from the true spirit and scope of the invention as defined in the appended claims.

What is claimed:

1. A method of determining noninvasively and in vivo one or more unknown values of known characteristics, such as the concentration of an analyte, of a biological fluid in a mammal, said method comprising the steps of:

(a) irradiating in vivo and noninvasively said biological fluid having said unknown values of said known characteristics with infrared energy having at least several wavelengths so that there is differential absorption of at least some of said wavelengths by said biological fluid as a function of said wavelengths and said characteristics, said differential absorption causing intensity variations of said wavelengths incident from said biological fluid as a function of said wavelengths and said unknown values of said known characteristics;
   (b) measuring said intensity variations from said biological fluid; and
   (c) calculating said unknown values of said known characteristics in said biological fluid from said measured intensity variations utilizing an algorithm and a mathematical calibration model, said algorithm including all independent sources of intensity variations v. wavelengths information obtained from irradiating a set of samples in which said values of said known characteristics are known, said algorithm also including more wavelengths than samples in said set of samples, said model being constructed from said set of samples and being a function of said known values and characteristics and said intensity variations v. wavelengths information obtained from irradiating said set of samples.

2. The method as set forth in claim 1, wherein said set of samples is irradiated in vivo and noninvasively.

3. The method as set forth in claim 1, wherein said infrared energy is near infrared energy.

4. The method as set forth in claim 1, wherein said algorithm is selected from the group including partial least squares and principal component regression.

5. The method as set forth in claim 1, wherein said biological fluid is irradiated by directing said infrared energy to be incident on a portion of said mammal which includes said biological fluid, so that said biological fluid partially absorbs said incident infrared energy.

6. The method as set forth in claim 5, wherein said infrared energy incident on said portion of said mammal passes through said portion.

7. The method as set forth in claim 6, wherein said portion is a digit.

8. The method as set forth in claim 5, wherein said infrared energy incident on said portion of said mammal is partially absorbed by said portion and partially diffusely reflected from said portion.

9. The method as set forth in claim 8, wherein said portion is a head.

10. The method as set forth in claim 5, wherein said irradiating is accomplished by coupling said infrared energy to said portion of said mammal by a fiber optic device.

11. The method as set forth in claim 10, wherein said infrared energy from said portion of said mammal is transmitted from said portion by said fiber optic device.

12. The method as set forth in claim 10, wherein said infrared energy from said portion of said mammal is transmitted by a second fiber optic device.

13. The method as set forth in claim 11, further including the step of detecting outlier samples in said set of samples.

14. The method as set forth in claim 13, wherein said detection of outlier samples in said set includes the step of comparing said intensity v. wavelength responses of each sample in said set to said model, the comparing step yielding a measure of the magnitude of the difference between said intensity v. wavelength responses of each of said samples and said model.

15. The method as set forth in claim 14, further including performing a statistical test to indicate the probability of said magnitude being caused by random chance, and classifying as outliers those of said samples in said set having an excessively low probability.

16. The method as set forth in claim 15 wherein the statistical test is the F ratio test.

17. The method as set forth in claim 13, wherein said detection of outlier samples in said set includes the step of comparing said known values of said characteristics of each sample in said set to the calculated value of said characteristic, said calculated value being based on an estimate derived from said model of said value of said characteristic for each said sample to determine a measure of the magnitude of the difference between said known value of said characteristic and said calculated value of said characteristic.

18. The method as set forth in claim 17, further including performing a statistical test to indicate the probability of said magnitude being caused by random chance, and classifying as outliers those of said samples in said set having an excessively low probability.

19. The method as set forth in claim 18, wherein the statistical test is the F ratio test.

20. The method as set forth in claim 11, further including the step of determining whether said intensity variations v. wavelengths response of said biological fluid with unknown values of said known characteristics is an outlier.

21. The method as set forth in claim 20, wherein said determination of whether said intensity variations v. wavelengths response of said biological fluid is an outlier includes the step of comparing said intensity variations v. wavelengths from said biological fluid to said model, the comparing step yielding a measure of the magnitude of the difference between said intensity variations v. wavelengths of said biological fluid and said model.

22. The method as set forth in claim 21, further including performing a statistical test to indicate the probability of said magnitude being caused by random chance, and classifying as outliers those of said values having an excessively low probability.

23. The method as set forth in claim 22, wherein the statistical test is the F ratio test.

24. The method as set forth in claim 1, wherein said known characteristics are minor components of said biological fluid and said unknown values are less than 2.0 weight percent of said biological fluid.

25. A method of determining invasively and in vivo one or more unknown values of known characteristics, such as the concentration of an analyte, of a biological fluid in a mammal, said method comprising the steps of:
(a) coupling invasively and in vivo a source of infrared energy with an internal portion of said mammal;
(b) irradiating in vivo and invasively said biological fluid having said unknown values of said known characteristics with said infrared energy having at least several wavelengths so that there is differential absorption of at least some of said wavelengths by said biological fluid as a function of said wavelengths and said characteristics, said differential absorption causing intensity variations of said wavelengths incident from said biological fluid as a function of said wavelengths and said characteristics having unknown values;
(c) measuring said intensity variations from said biological fluid; and
(d) calculating said unknown values of said known characteristics in said biological fluid from said measured intensity variations from said biological fluid utilizing an algorithm and a mathematical calibration model, said algorithm including all independent sources of intensity variations v. wavelengths information obtained from irradiating a set of samples in which said known values of said known characteristics are known, said algorithm also being capable of using more wavelengths than samples in said set of samples, said model being constructed from said set of samples and being a function of said known values and characteristics and said intensity variations v. wavelengths information obtained from irradiating said set of samples.

26. The method as set forth in claim 25, wherein said samples are irradiated invasively and in vivo.

27. The method as set forth in claim 25, wherein said algorithm is selected from the group including partial least squares and principal component regression.

28. The method as st forth in claim 25, wherein said source of infrared energy is coupled with said mammal by at least partially implanting a fiber optic device in said mammal.

29. The method as set forth in claim 28, wherein at least a portion of said fiber optic device is used as an attenuated total reflectance (ATR) device.

30. The method as set forth in claim 29, comprising passing said fiber optic device through a portion of said mammal.

31. The method as set forth in claim 25, comprising implanting an ATR crystal in said mammal, said ATR device being coupled to said source of infrared energy.

32. The method as set forth in claim 25, comprising implanting said source of infrared energy and apparatus for measuring said intensity variations in said mammal proximate to a supply of said biological fluid.

33. The method as set forth in claim 32, comprising positioning said source of infrared energy and said measuring apparatus on opposite sides of said biological fluid.

34. The method as set forth in claim 33, comprising positioning said source of infrared energy and said measuring apparatus on opposite sides of at least one blood vessel of said mammal.

35. The method as set forth in claim 25, wherein said infrared energy is either in the mid-infrared or near-infrared spectrum.

36. The method as set forth in claim 25, further including the step of detecting outlier samples in said set of samples.

37. The method as set forth in claim 36, wherein said detection of outlier samples in said set includes the step of comparing said intensity v. wavelength responses of each sample in said set to said model to determine a measure of the magnitude of the difference between said intensity v. wavelength responses of each of said samples and said model.

38. The method as set forth in claim 37, further including performing a statistical test to indicate the probability of said magnitude being caused by random chance, and classifying as outliers those of said samples in said set having an excessively low probability.

39. The method as set forth in claim 38, wherein the statistical test is the F ratio test.

40. The method as set forth in claim 25, wherein said detection of outlier samples in said set includes the step of comparing said known values of said characteristics of each sample in said set to the calculated value of said characteristic, said calculated value being based on an estimate derived from said model of said value of said characteristic for each said sample to determine a measure of the magnitude of the difference between said known value of said characteristic and said calculated value of said characteristic.

41. The method as set forth in claim 40, further including performing a statistical test to indicate the probability of said magnitude being caused by random chance, and classifying as outliers those of said samples in said set having an excessively low probability.

42. The method as set forth in claim 41, wherein the statistical test is the F ratio test.

43. The method as set forth in claim 25, further including the step of determining whether said intensity variations v. wavelengths of said biological fluid with unknown values of said known characteristics is an outlier.

44. The method as set forth in claim 43, wherein said determination of whether said intensity variations v. wavelengths of said biological fluid is an outlier includes the step of comparing said intensity variations v. wavelengths from said biological fluid to said model, said comparing step yielding a measure of the magnitude of the difference between said intensity variations v. wavelengths between said biological fluid and said model.

45. The method as set forth in claim 44, further including performing a statistical test to indicate the probability of said magnitude being caused by random chance, and classifying as outliers those of said values having an excessively low probability.

46. The method as set forth in claim 45, wherein the statistical test is the F ratio test.

47. The method as set forth in claim 25, wherein said known characteristics are minor components of said biological fluid and said unknown values are less than 2.0 weight percent of said biological fluid.

48. A method of determining in vitro one or more unknown values of known characteristics, such as the concentration of an analyte, of biological fluid, said method comprising the steps of:
   (a) irradiating in vitro said biological fluid having said unknown values of said known characteristics with infrared energy having at least several wavelengths so that there is differential absorption of at least some of said wavelengths by said biological fluid as a function of said wavelengths and said characteristics, said differential absorption causing intensity variations of said wavelengths incident from said biological fluid as a function of said wavelengths and said characteristics having unknown values;
   (b) measuring said intensity variations from said biological fluid; and
   (c) calculating said unknown values of said known characteristics in said biological fluid from said measured intensity variations from said biological fluid, utilizing an algorithm and a mathematical calibration model, said algorithm including all independent sources of intensity variations v. wavelengths information obtained from irradiating a set of samples in which said values of said known characteristics are known, said algorithm also including more wavelengths than samples in said set of samples, said model being constructed from said set of samples and being a function of said known values and characteristics, said intensity variations v. wavelengths information being obtained by irradiating said set of samples.

49. The method as set forth in claim 48, wherein said samples are irradiated in vitro.

50. The method as set forth in claim 48, wherein said algorithm is selected from the group including, partial least squares and principal component regression.

51. The method as set forth in claim 48, further including the step of detecting outlier samples in said set of samples.

52. The method as set forth in claim 48, further including the step of determining whether said intensity variations v. wavelengths response of said biological fluid with unknown values of said characteristics is an outlier.

53. The method as set forth in claim 48, wherein said known characteristics are minor components of said biological fluid and said unknown values are less than 2.0 weight percent of said biological fluid.

54. Apparatus for determining at least one unknown value of a known characteristic, such as the concentration of an analyte, in a biological fluid, said apparatus comprising:
   (A) a source of infrared energy having at least several wavelengths;
   (B) means for coupling said at least several wavelengths of said infrared energy to said biological fluid to enable said biological fluid to differentially absorb at least some of said wavelengths, said differential absorption causing intensity variations of said infrared energy incident from said biological fluid as a function of said at least several wavelengths of said energy and said unknown value of said known characteristic;
   (C) means for measuring said intensity variations; and
   (D) computer means including:
      i. a stored model constructed from a set of samples in which the values of said known characteristic are known, said model being a function of said known values from said set of samples and intensity v. wavelength information obtained from said set of samples, and
      ii. an algorithm including (a) all independent sources of said intensity variations v. said wavelengths information from both said set of samples and said biological fluid and (b) more wavelengths than samples, said algorithm utilizing said model for calculating said unknown value of said known characteristic of said biological fluid from said measured intensity variations from said biological fluid.

55. The apparatus as set forth in claim 54, further including means for determining whether said intensity variations v. wavelength of said known characteristic in said biological fluid is an outlier.

56. The apparatus as set forth in claim 54, wherein said means for coupling includes an attenuated total reflectance (ATR) device.

57. The apparatus as set forth in claim 56, further including a flow cell, said ATR device being positioned in said cell for in vitro sampling.

58. The apparatus as set forth in claim 56, wherein said ATR device includes a biocompatible coating on at least a portion thereof for enabling said portion of said ATR device to contact said biological fluid in vivo.

59. The apparatus as set forth in claim 54, wherein said means for coupling includes a fiber optic device.

60. The apparatus as set forth in claim 59, wherein a portion of said fiber optic device forms an ATR device.

61. The apparatus as set forth in claim 59, wherein said fiber optic device includes a portion for transmitting said infrared energy to said biological fluid and a separate portion for transmitting said infrared energy from said biological fluid to said apparatus.

62. The apparatus as set forth in claim 54, wherein said apparatus includes a first portion adapted to be positioned on one side of an in vivo source of biological fluid and a second portion adapted to be positioned on another side of said in vivo source of biological fluid.

63. The apparatus as set forth in claim 54, wherein said means for coupling includes means for transmitting said infrared energy to an in vivo source of said biological fluid and means for measuring diffuse infrared reflection from said in vivo source.

64. The apparatus as set forth in claim 54, further including means for transmitting signals from said computer means to a means for changing said value of said known characteristic.

65. The apparatus as set forth in claim 64, wherein said means for changing is an insulin pump.

66. The apparatus of claim 54, wherein said means for measuring said intensity variations includes an array of infrared sensors, means for frequency dispersing said intensity variations of said at least several wavelengths onto said sensors, different ones of said sensors being provided for different ones of said at least several wavelengths, so that said different ones of said sensors derive different electric signals.

67. The apparatus of claim 66, wherein said array includes multiple individual filters, each having a bandpass for each one of said at least several wavelengths, said filters being positioned relative to said sensors so that said infrared energy passed through each of said filters is incident on a corresponding one of said sensors.

68. The apparatus of claim 66, wherein said array includes a sheet of infrared gradient wavelength responsive material having areas positioned relative to said sensors so that said infrared energy passed through different areas of said sheet is incident on a corresponding one of said sensors.

69. The apparatus of claim 66, wherein each of said sensors is constructed to be responsive to a different one of said at least several wavelengths.

70. A method of determining in vivo at least one unknown concentration of a known characteristic in a biological fluid in a mammal, said characteristic being a trace component in said biological fluid, said concentration being less than 2.0 weight percent of said biological fluid, said method comprising:

(a) irradiating in vivo said biological fluid having said unknown concentration of said known characteristic with infrared energy having said at least several wavelengths so that there is differential absorption of at least some of said wavelengths by said biological fluid as a function of said wavelengths and said unknown concentration, said differential absorption causing intensity variations of said wavelengths incident from said biological fluid as a function of said wavelengths and said unknown concentration;

(b) measuring said intensity variations from said biological fluid;

(c) calculating said unknown concentration in said biological fluid from said measured intensity variations from said biological fluid utilizing an algorithm and a mathematical calibration model, said algorithm including all independent sources of intensity variations v. wavelengths information obtained from irradiating a set of samples in which the concentrations of said known characteristic are known, said algorithm including more wavelengths than samples in said set of samples, said model being constructed from said set of samples and being a function of said known concentrations of said known characteristic and the intensity variations v. wavelengths information obtained from irradiating said set of samples; and (d) determining whether said intensity variations v. wavelengths of said biological fluids is an outlier.

71. The method as set forth in claim 70, wherein said known characteristic is glucose.

* * * * *

UNITED STATES PATENT AND TRADEMARK OFFICE
CERTIFICATE OF CORRECTION

PATENT NO. : 4,975,581
DATED : December 4, 1990
INVENTOR(S) : Mark R. Robinson et al It is certified that error appears in the above-indentified patent and that said Letters Patent is hereby corrected as shown below:

Column 1, line 7, after the title of the invention please add the following Government License Rights Statement:

--The United States Government has a paid-up license in this invention and the right in limited circumstances to require the patent owner to license others on reasonable terms as provided for by the terms of Contract Number DE-AC04-76DP00789 awarded by the United States Department of Energy.--

Signed and Sealed this

Twenty-fifth Day of January, 1994

Attest:

BRUCE LEHMAN

Attesting Officer

Commissioner of Patents and Trademarks